United States Patent
Slepicka et al.

(10) Patent No.: US 9,656,052 B2
(45) Date of Patent: *May 23, 2017

(54) ACOUSTIC LINE TRACING SYSTEM AND METHOD FOR FLUID TRANSFER SYSTEM

(71) Applicants: Baxter International Inc., Deerfield, IL (US); Baxter Healthcare S.A., Glattpark (Opfikon) (CH)

(72) Inventors: James Scott Slepicka, Genoa City, WI (US); Thomas Edward Dudar, Palatine, IL (US)

(73) Assignees: BAXTER INTERNATIONAL INC., Deerfield, IL (US); BAXTER HEALTHCARE S.A., Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/133,483

(22) Filed: Apr. 20, 2016

(65) Prior Publication Data

US 2016/0228688 A1 Aug. 11, 2016

Related U.S. Application Data

(63) Continuation of application No. 13/837,417, filed on Mar. 15, 2013, now Pat. No. 9,359,885.

(51) Int. Cl.
*A61M 5/172* (2006.01)
*G01N 29/24* (2006.01)
(Continued)

(52) U.S. Cl.
CPC ............ *A61M 39/10* (2013.01); *A61M 5/142* (2013.01); *A61M 5/14212* (2013.01); *A61M 5/172* (2013.01); *A61M 39/08* (2013.01); *E21B 47/091* (2013.01); *G01N 29/2437* (2013.01); *A61M 5/14* (2013.01); *A61M 2039/087* (2013.01); *A61M 2039/1005* (2013.01);
(Continued)

(58) Field of Classification Search
CPC ... E21B 47/091; A61M 5/14212; A61M 5/14; A61M 39/08; A61M 2039/087; A61M 2205/14; A61M 2205/3375; A61M 2205/6009
USPC ......................................... 73/649; 166/255.2
See application file for complete search history.

(56) References Cited

U.S. PATENT DOCUMENTS

| | | |
|---|---|---|
| 4,526,404 A | 7/1985 | Vazquez |
| 5,048,870 A | 9/1991 | Mangini et al. |

(Continued)

FOREIGN PATENT DOCUMENTS

| | | |
|---|---|---|
| WO | 03098534 A1 | 11/2003 |
| WO | 2005116790 A2 | 8/2005 |

(Continued)

*Primary Examiner* — J M Saint Surin
(74) *Attorney, Agent, or Firm* — Greer, Burns & Crain, Ltd.

(57) ABSTRACT

An acoustic line tracing system for tracing a fluid transfer system tubing line includes an acoustic receiver operably connectable to the tubing line and configured to receive the vibratory signal. The acoustic receiver includes a vibration sensor disposed to contact the tubing line and configured for detecting vibration of the surface of the tubing line caused by the vibratory signal, and an indicator producing at least one of an audio and a visual cue when the vibration sensor detects the vibratory signal.

19 Claims, 3 Drawing Sheets

(51) Int. Cl.
*A61M 5/142* (2006.01)
*A61M 39/08* (2006.01)
*E21B 47/09* (2012.01)
*A61M 39/10* (2006.01)
*A61M 5/14* (2006.01)

(52) U.S. Cl.
CPC ............... *A61M 2039/1044* (2013.01); *A61M 2205/0294* (2013.01); *A61M 2205/14* (2013.01); *A61M 2205/3375* (2013.01); *A61M 2205/581* (2013.01); *A61M 2205/583* (2013.01); *A61M 2205/587* (2013.01); *A61M 2205/6009* (2013.01); *G01N 2291/0289* (2013.01)

(56) References Cited

U.S. PATENT DOCUMENTS

| | | | |
|---|---|---|---|
| 5,090,779 | A | 2/1992 | Kramer |
| 5,180,287 | A | 1/1993 | Natwick et al. |
| 5,329,927 | A | 7/1994 | Gardineer et al. |
| 5,782,495 | A | 7/1998 | Grosskopf et al. |
| 5,799,981 | A | 9/1998 | Tung et al. |
| 5,855,395 | A | 1/1999 | Foote et al. |
| 5,958,536 | A | 9/1999 | Gelsinger et al. |
| 5,974,708 | A | 11/1999 | Webb et al. |
| 6,035,568 | A | 3/2000 | Grosskopf et al. |
| 6,142,008 | A | 11/2000 | Cole et al. |
| 6,410,111 | B1 | 6/2002 | Roth et al. |
| 6,468,242 | B1 | 10/2002 | Wilson et al. |
| 7,092,797 | B2 | 8/2006 | Gaines et al. |
| 7,455,662 | B2 | 11/2008 | Kraushaar |
| 8,266,878 | B2 | 9/2012 | Luciano, Jr. et al. |
| 8,317,770 | B2 | 11/2012 | Miesel et al. |
| 8,571,881 | B2 | 10/2013 | Rousso et al. |
| 8,597,271 | B2 | 12/2013 | Langan et al. |
| 8,808,249 | B2 | 8/2014 | Langan et al. |
| 8,962,707 | B2 | 2/2015 | Singh |
| 9,359,885 | B2 * | 6/2016 | Slepicka ........... A61M 5/14212 |
| 2002/0038392 | A1 | 3/2002 | De La Huerga |
| 2002/0056989 | A1 | 5/2002 | Lewis-Leander |
| 2002/0077582 | A1 | 6/2002 | Mehdi et al. |
| 2006/0081255 | A1 | 4/2006 | Miller et al. |
| 2006/0265246 | A1 | 11/2006 | Hoag |
| 2007/0088286 | A1 | 4/2007 | Brier |
| 2007/0107517 | A1 | 5/2007 | Arnold et al. |
| 2007/0208595 | A1 | 9/2007 | Ohmura et al. |
| 2007/0233520 | A1 | 10/2007 | Wehba et al. |
| 2008/0046288 | A1 | 2/2008 | Menon et al. |
| 2008/0131362 | A1 | 6/2008 | Rousso et al. |
| 2009/0053071 | A1 | 2/2009 | Wang et al. |
| 2010/0094653 | A1 | 4/2010 | Tribble et al. |
| 2011/0071844 | A1 | 3/2011 | Cannon et al. |
| 2013/0289496 | A1 | 10/2013 | Langan et al. |
| 2014/0067425 | A1 | 3/2014 | Dudar et al. |
| 2014/0130909 | A1 | 5/2014 | Dudar et al. |
| 2014/0326629 | A1 | 11/2014 | Langan et al. |

FOREIGN PATENT DOCUMENTS

| | | |
|---|---|---|
| WO | 2005097246 A1 | 10/2005 |
| WO | 2006122167 A2 | 11/2006 |
| WO | 2014055434 A1 | 4/2014 |

* cited by examiner

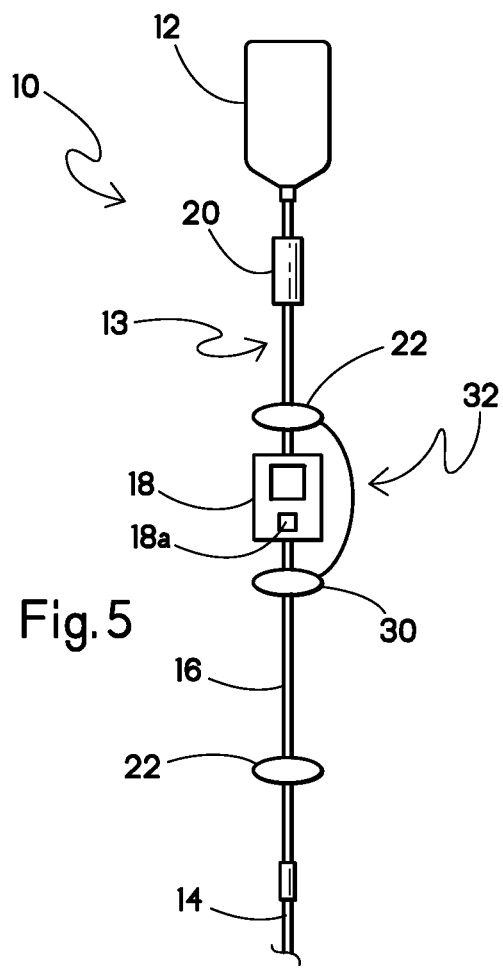

ACOUSTIC LINE TRACING SYSTEM AND METHOD FOR FLUID TRANSFER SYSTEM

CROSS-REFERENCE

The present application is a Continuation application of and claims priority to U.S. patent application Ser. No. 13/837,417 filed Mar. 15, 2013, which is incorporated herein by reference.

FIELD OF THE INVENTION

The present invention relates to a system and method for tracing a particular tubing set from end to end, more particularly to a system and method that uses acoustic vibration to trace a tubing system for fluid transfer, and even more particularly to a system and method for tracing tubing systems used in the medical industry for transfer of fluids, such as intravenous infusion tubing, using acoustic vibration.

BACKGROUND

Errors in administration of medication through a fluid transfer system, such as a patient infusion system or an automatic compounder, can result from many causes, including misconnections. Accordingly, to reduce the potential for such errors, professional guidelines and/or standard operating procedures require clinicians, such as nurses and pharmacists, to perform "line management," also known as line tracing, numerous times throughout their working shifts. In the case of an automatic compounder, line management involves verifying each medication source container is routed through tubing to the correct input of the mixing manifold and pump. In the case of a patient infusion system, line management involves verifying that each medication source container, typically a bag, bottle, or syringe, is routed through tubing to the correct catheter, and that the tubing is associated with the correct pump channel (if an infusion pump is used). The activity further includes verifying that it is safe to join two or more tubing segments containing different medications and/or flowing at different rates. By way of example, a nurse or other clinician may perform line management for each patient when starting a shift, when receiving a patient from another facility, another area of the hospital, or a different clinician, and just prior to administration of an intravenous medication. Repeated performance of the detailed line management procedure imposes a time burden on the clinicians, and is prone to errors, particularly as the complexity of a patient's overall infusion tubing system increases. That is, multiple tubing sets, medications, junctions, access ports, pump channels, and catheters increase the amount of time required to perform line management and also introduce additional opportunities for error in line management.

To facilitate line management, clinicians often manually label infusion setups at various locations throughout the tubing system. Generally, the labeling is crude, using materials on hand such as medical tape wrapped around the tubing and labeled with identifying information such as the medication name. This labeling is repeated at several points throughout the system. For example, labels may be placed at the spike end of a tubing set, at the catheter connection, at each access port and junction, on the roller clamp and slide clamp, on the catheter, on the pump channel itself, and on the medication container. When applying such labels, a clinician manually slides his or her hand along the tube, progressing from a first tube end to a second tube end, and labeling desired points along the length of the tube.

Line management systems should be capable of identifying the correct line, catheter, and connector prior to connecting any new medicine container and line or prior to injecting a medication into an existing access port. Additionally, the system should allow a user to correctly identify a container and its corresponding line and pump interface before loading the tubing line into the pump. The system should also maintain clear physical and visual association among the container, line, pump, and catheter. Proposed systems for facilitating the line management process include color coding of the tubing sets used in the infusion system, use of the tubing as an optical waveguide similar to glass or plastic optical fibers, and use of electrically conducting wires embedded in the wall of the tubing. Each of these solutions provides some advantages, but a primary disadvantage to each proposal is that it would require development of a specialized tubing set.

Accordingly, there is a need for a system that facilitates accurate line management without the need for development of new tubing systems.

SUMMARY

An improved acoustic line tracing system addresses these needs. The acoustic sensor system allows for accurate tracing of a line, without the need for developing a specialized tubing set. Accordingly, existing tubing sets, with known physical characteristics can be used with the acoustic tracing system.

In a first aspect, an acoustic line tracing system for tracing a fluid transfer system tubing line includes an acoustic receiver operably connectable to the tubing line and configured to receive a vibratory signal. The acoustic receiver includes a vibration sensor disposed to contact the tubing line and configured for detecting vibration of the surface of the tubing line caused by the vibratory signal, and an indicator producing at least one of an audio and a visual cue when the vibration sensor detects the vibratory signal.

In another aspect of the invention, an acoustic line tracing system for verifying continuity of a tubing set in an infusion system includes a first acoustic receiver connectable to the tubing line and configured for receiving a vibratory signal. The first acoustic receiver has a vibration sensor disposed to contact the tubing line and configured for detecting vibration of the surface of the tubing line caused by the vibratory signal. A signal transmitter operatively contacts the tubing set and is electrically coupled with the first acoustic receiver. The signal transmitter is configured for generating acoustic vibrations in the tubing line when the sensor detects a vibratory signal. A second acoustic receiver is connectable to the tubing line and configured for receiving the acoustic vibrations generated by said signal transmitter. The second acoustic receiver includes a sensor disposed to contact the tubing line and configured for detecting vibrations in the surface of the tubing line caused by the acoustic vibrations, and an indicator producing at least one of an audio and a visual cue when the vibration sensor detects the vibrations. The first acoustic receiver and the signal transmitter are separated by at least one vibration dampening component.

In still another aspect of the invention, a method for tracing a tubing set to determine set continuity includes a step of providing an acoustic receiver in contact with the tubing set at a first position along the tubing set. The acoustic receiver has a vibration sensor operatively that is in contact with the tubing set and capable of sensing vibrations in the tubing set, and an indicator capable of producing at least one of an audio and a visual cue when said vibration sensor detects the vibrations. The method further includes a step of inducing a vibratory signal at a second position along the tubing set, and a step of detecting, using the provided acoustic receiver, whether or not the vibratory signal is received at the first position along the tubing set. The method also includes a step of determining whether the tubing set is continuous between the first position and the second position, where the tubing set is determined to be continuous if the vibration sensor detects the vibratory signal at the detecting step. The indicator produces the audio and/or visual cue when it is determined that the tubing set is continuous.

In one embodiment, an acoustic line tracing system is provided for tracing a fluid transfer system tubing line. Included in the tracing system are an infusion pump, and a first acoustic receiver operably connectable to the tubing line and configured to receive a vibratory signal. The first acoustic receiver includes a first vibration sensor disposed to contact the tubing line, and the first vibration sensor is configured for detecting vibration of the surface of the tubing line caused by the vibratory signal. A signal transmitter operatively contacts the tubing set and is electrically coupled with the first acoustic receiver, and the signal transmitter is configured for generating acoustic vibrations in the tubing line when the first vibration sensor detects the vibratory signal. The first acoustic receiver is upstream from the infusion pump and the signal transmitter is downstream from the infusion pump for reducing dampening of the vibratory signal by the infusion pump.

In another embodiment, an acoustic line tracing system is provided for verifying continuity of a tubing set in an infusion system. Included in the line tracing system are an infusion pump, and a first acoustic receiver connectable to the tubing line and configured for receiving a vibratory signal. The first acoustic receiver includes a first vibration sensor disposed to contact the tubing line, and the first vibration sensor is configured for detecting vibration of the surface of the tubing line caused by the vibratory signal. A signal transmitter operatively contacts the tubing set and electrically coupled with the first acoustic receiver, and the signal transmitter is configured for generating acoustic vibrations in the tubing line when the first vibration sensor detects the vibratory signal. The first acoustic receiver and said signal transmitter are separated by the infusion pump for reducing dampening of the vibratory signal by the infusion pump.

In yet another embodiment, a method for determining continuity of a tubing set includes steps of providing: a first acoustic receiver operably connectable to the tubing line and configured for receiving a vibratory signal, the first acoustic receiver including a first vibration sensor disposed to contact the tubing line, the first vibration sensor being configured for detecting vibration of the surface of the tubing line caused by the vibratory signal. A signal transmitter operatively contacts the tubing set and electrically coupled with said first acoustic receiver, and the signal transmitter is configured for generating acoustic vibrations in the tubing line when the first vibration sensor detects the vibratory signal. The first acoustic receiver is upstream from an infusion pump and the signal transmitter is downstream from the infusion pump to reduce dampening of the vibratory signal by the infusion pump.

BRIEF DESCRIPTION OF THE DRAWINGS

FIG. 5 shows the infusion system of FIG. 2, and a removable acoustic line receiver including a relay.

DETAILED DESCRIPTION

Figure 1:
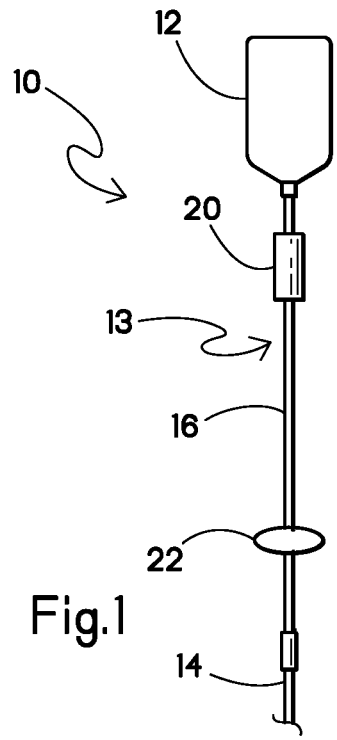
FIG. 1 shows an infusion system including a removable acoustic receiver according to an embodiment of the present invention.
Figure 2:
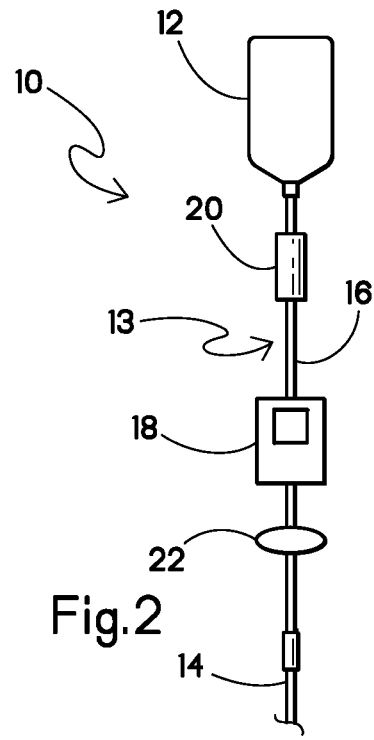
FIG. 2 shows an infusion system including an infusion pump and a removable acoustic receiver according to an embodiment of the present invention.

Referring now to FIGS. 1 and 2, a fluid transfer system is shown schematically as infusion system 10. While FIGS. 1 and 2 show the fluid transfer system as patient infusion system 10, those of skill in the art will recognize that other fluid transfer systems, such as automatic compounder systems, are within the scope of the present invention. The infusion system 10 includes a medication container 12, a catheter 14 for connection to a patient, and a tubing set 16 providing fluid communication between the medication container 12 and the catheter 14. The infusion system 10 can be a so-called "gravity-fed" pumpless system as shown in FIG. 1, or optionally includes an infusion pump 18 for pumping the medication from the container 12 through the tubing set 16 and catheter 14 into a patient as shown in FIG. 2. While the systems 10 shown in FIGS. 1 and 2 include equipment for delivering a single medication for clarity, those of skill in the art will recognize that an infusion system may include multiple containers, catheters, pumps, and tubing sets.

The medication container 12 can be, for example, a bag, bottle, syringe, or other standard container used to contain liquid medications. There is no particular restriction regarding what containers may be used. A drip chamber 20 is preferably disposed directly downstream from the medication container 12. The drip chamber 20 allows gas to separate from fluid exiting the medication container 12, thus helping to prevent an air embolism, and also helps a clinician estimate the flow rate of the medication by allowing the clinician to count the number of drops of the medication that enter the drip chamber 20 in a given period of time.

The catheter 14 can be any standard equipment for use with a patient. The catheter 14 may be, for example, a temporary catheter inserted into a peripheral vein, a peripherally inserted central catheter, a central venous catheter, or other catheter known to those in the art. Likewise, the tubing set 16 is any standard tubing set used to connect the medication container 12 to the catheter 14.

As shown in FIG. 2, the infusion pump 18 is any known pump used to administer fluid intravenously. The pump 18 is used to help regulate fluid flow through the system 10, and may be used to vary an infusion rate based on, for example time and/or patient demand. The pump 18 is positioned between the drip chamber 20 and the catheter 14, and may include one or more "channels," with each channel used to regulate fluid flow from a distinct medication container through a distinct tubing set.

FIGS. 1 and 2 each show at least one acoustic receiver 22 connected to an exterior surface of the tubing set 16. The acoustic receiver 22 is a device capable of detecting acoustic waves transmitted through the tubing set 16. The receiver 22 is preferably removably secured to the tubing set 16, such that a clinician can position the receiver at any desired position along the length of the tubing set, and can move the receiver from one tubing set to another as desired. While FIG. 2 shows the acoustic receiver 22 as a separate device, artisans will recognize that the receiver can optionally be incorporated into the pump 18 as an integrated acoustic receiver disposed at one or both of the upstream and downstream sides of the pump without departing from the scope of the invention. Alternatively, the receiver 22 is optionally formed as an integral portion of the tubing set 16, disposed near the medication container 12 and/or near the catheter 14. Alternatively, the receiver 22 is optionally formed as an integral portion of the infusion system 10, including the medication container 12 and/or the catheter 14.

Figure 3:
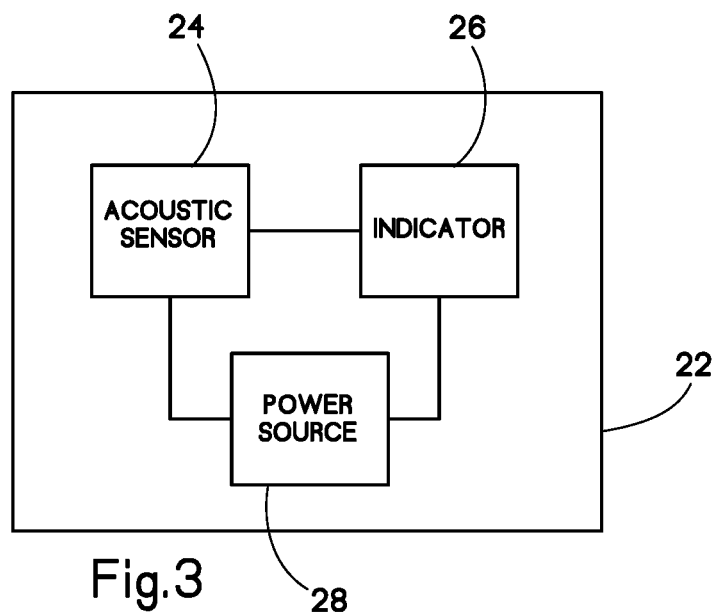
FIG. 3 shows a schematic drawing of an acoustic receiver as shown in FIGS. 1 and 2.

As shown in FIG. 3, the acoustic receiver 22 includes a sensor 24, an indicator 26, and a power source 28. The sensor 24, such as a vibration sensor is disposed in contact with the tubing set 16, and is used to detect an acoustic vibratory signal transmitted through the tubing set 16. In the preferred embodiment, the sensor 24 is a transducer capable of converting vibrations from the tubing set 16 into an electrical signal. For example, the sensor 24 is optionally a microphone such as a contact microphone or other piezoelectric device.

The sensor 24 is electrically connected to the indicator 26, which provides at least one of an audio and a visual or other indication when the sensor 24 detects sound waves. The indicator 26 is preferably a small indicator light such as a light emitting diode, a small loudspeaker capable of emitting an audible tone, or other device capable of providing an observable signal to a clinician.

The power source 28 provides power to the receiver 22. The power source 28 is preferably a compact portable power source such as a battery. However, other sources, such as a connection to mains power, photovoltaic panels, and the like may be used without departing from the scope of the invention.

The receiver 22 is preferably removably connected to the tubing itself and/or any component of the tubing set 16, such as the drip chamber 20 and/or access ports. Alternatively, the receiver 22 can be connected to other portions of the infusion system 10, including the medication container 12 or the catheter 14. This connection is formed by, for example a spring-biased clamp. The force exerted on the tubing set 16 by the receiver 22 is desirably sufficient for maintaining steady contact between the sensor 24 and the tubing set, so that an accurate reading can be performed. However, the biasing force retaining the receiver 22 in place should not be so strong as to occlude the tubing set 16.

Turning now to FIG. 5, the signal sensed by the acoustic receiver 22 is preferably provided, for example, by a signal transmitter 30 preferably removably connected to the tubing set. The transmitter 30 may be any device capable of producing a vibratory acoustic signal, preferably an ultrasound signal having a frequency greater than 20 kHz. In the preferred embodiment, the transmitter 30 includes a piezoelectric device configured for generating ultrasonic acoustic vibrations. The transmitter 30 can be a separate device, or optionally can be incorporated into the tubing set 16. Alternatively, the transmitter 30 can optionally be attached to or formed integrally with other elements of the infusion system 10, including the medication container 12 and/or the catheter 14. As shown in FIG. 5, the transmitter 30 can also optionally be incorporated into the infusion pump 18 as an integrated signal transmitter 18a. While FIG. 5 shows integrated signal transmitter 18a disposed on the downstream side of the pump 18, those of skill in the art will recognize that an integrated signal transmitter can be disposed at one or both of the upstream and downstream sides without departing from the scope of the invention. Alternatively, a pumping mechanism of the infusion pump 18 can be the signal transmitter 30. While in the depicted embodiment, the signal transmitter 30 is separate from the acoustic receiver 22, it is also contemplated that the acoustic receiver 22 is also optionally capable of generating an acoustic vibratory signal, thus operating as a signal transmitter/receiver or "transceiver". As a further alternative, the vibratory signal may be generated manually, for example by a clinician tapping the tubing set using, for example, a finger or other implement. The vibratory acoustic signal is preferably applied at a location 13 distant from the receiver 22, so that opposite ends of the tubing set 16 are determined to be continuous. As examples, FIG. 1 shows the vibratory signal can be applied to the tubing set 16 at the location 13 disposed proximate to the medication container 12, while the receiver 22 is positioned proximate to the catheter 14; FIG. 2 shows the vibratory signal applied at a location 13 downstream from the pump 18, with the receiver 22 positioned near the catheter 14; and FIG. 5 shows the vibratory signal applied at the position 13 near the medication bag, with a first receiver 22 positioned upstream of the pump 18.

Figure 4:
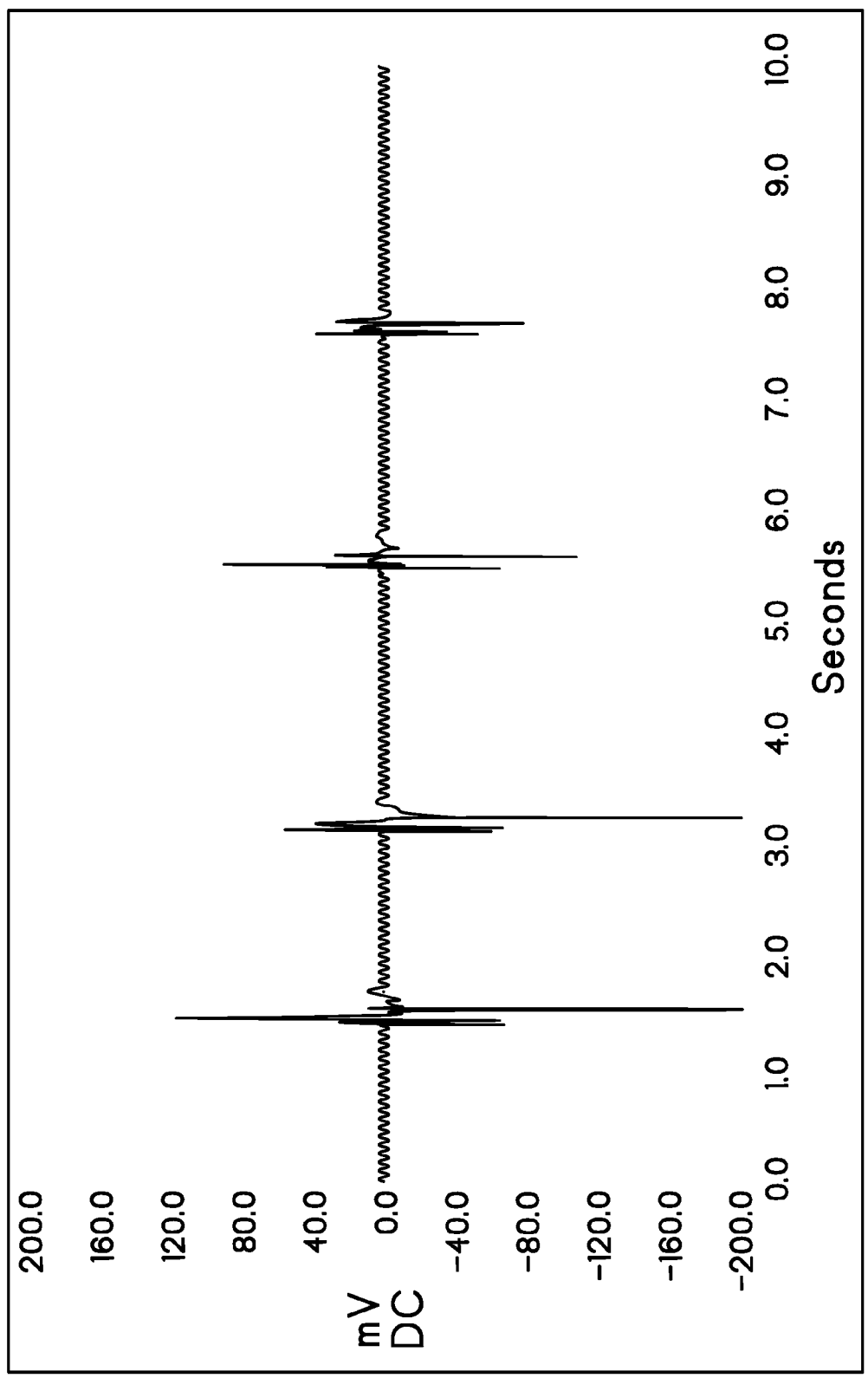
FIG. 4 shows a graph of a vibratory acoustic signal received by the acoustic receiver of FIG. 3.

In practice, to aid in creation of an infusion mapping, a vibratory signal is provided at a first end of the tubing set 16. The signal is optionally provided continuously or intermittently (e.g., a pulsed signal). The acoustic receiver 22 is then systematically connected to each of a plurality of candidate tubes at a second end of the infusion system 10, until the vibratory signal is detected by the sensor 24 at the tube which is in fluid communication with the tube coupled to the signal transmitter. FIG. 4 shows a graph indicating receipt of a pulsed signal by the sensor 24, such as by the signal transmitter 30 or by a clinician tapping on the tubing set 16. In response to the sensor 24 receiving the vibratory signal, the indicator 26 provides an indication to the clinician that the signal has been received. The clinician then knows that the tubing section 16 to which the acoustic receiver 22 is connected is continuous with the tubing section to which the vibratory signal is provided.

Referring now to FIG. 2, addition of the infusion pump 18 to the system 10 creates additional complications for acoustic continuity sensing. In particular, the infusion pump 18 may dampen the provided vibratory signal sufficiently that a signal provided on an upstream side of the pump cannot be accurately detected on a downstream side of the pump (or vice versa). One method of accommodating the dampening factor of the infusion pump 18 is to use a two-step process, whereby the receiver 22 is initially placed on the tubing set 16 near the catheter 14, and a vibratory signal is systematically transmitted from the location 13 associated with each pump channel output on the downstream side of the pump or pumps (if there are multiple pumps in the infusion system), one by one, until continuity is established on the downstream side of the infusion system. This allows the clinician to determine which pump channel is associated with the tubing set 16 near the catheter 14. Then, a vibratory signal is transmitted from the location 13 associated with the upstream side of the pump 18 on the same channel, and the receiver 22 is systematically moved from one tubing system to another near the medication containers 12 until the signal is received. This shows continuity from the medicine container 12 to the pump 18. In this way, continuity can be established fully from the medication container 12 to catheter 14 using only a single receiver 22 and a single transmitter 30, even with an intervening infusion pump 18. This is generally referred to as a "pump out" approach because the signals are transmitted from positions proximal to the pump in both upstream and downstream directions. The system and method can be streamlined when the upstream and downstream signal transmitters 30 and associated software are incorporated into the pump 18. In this case, only a single receiver 22 needs to be positioned by the clinician.

One of skill in the art will note that the above-listed steps are optionally performed in the opposite order, such that continuity from the medication container 12 to the pump 18 is determined before continuity from the pump to the catheter 14, without departing from the scope of the invention. Further, artisans will appreciate that the positions of the transmitter 30 and receiver 22 could be switched to generate a "pump in" workflow, such that signals are transmitted from the catheter 14 and the medication container 12, and received at the upstream and downstream sides of the pump 18. The system and method can be streamlined when the upstream and downstream acoustic receivers 22 and associated software are incorporated into the pump 18. In this case, only a single signal transmitter 30 needs to be positioned by the clinician. Further simplification is possible when finger taps are used in place of the signal transmitter 30.

Similarly, a "top down" workflow uses a signal transmitted from the medicine container and received at the pump upstream side, and a signal transmitted from the pump downstream side and received at the catheter. A "bottom up" workflow uses a signal transmitted from the catheter and received at the pump downstream side and a signal transmitted from the pump upstream side and received at the medicine container. The chart below shows the positioning of the transmitters and receivers with respect to the medication container, pump upstream side, pump downstream side, and catheter:

|  | Medication Container | Pump Upstream Side | Pump Downstream Side | Catheter |
| --- | --- | --- | --- | --- |
| "pump out" | Receiver | Transmitter | Transmitter | Receiver |
| "pump in" | Transmitter | Receiver | Receiver | Transmitter |
| "top down" | Transmitter | Receiver | Transmitter | Receiver |
| "bottom up" | Receiver | Transmitter | Receiver | Transmitter |

While each of the above configurations and workflows results in the same determination of continuity, different clinicians may find certain workflows more expedient and/or more intuitive. Accordingly, a system that allows for the flexibility to determine continuity in whichever way a clinician prefers is advantageous in that it encourages the clinicians to use the equipment, reducing the propensity for errors in line tracing and increasing the speed at which a line tracing can be performed.

Another method of accommodating the dampening factor of the infusion pump 18 is to use a relay 32. As shown in FIG. 5, the infusion system 10 optionally includes a relay 32 having the acoustic receiver 22 electrically coupled to the signal transmitter 30 via a wired or wireless connection. The relay is disposed such that the receiver and the transmitter are on opposite sides of the pump (i.e., the receiver 22 is disposed upstream, while the transmitter 30 is disposed downstream, or vice versa). Then, an acoustic signal is provided to the tubing set 16 on the side of the pump that includes the receiver. When the receiver 22 receives the provided signal, a corresponding signal is generated by the electrically coupled signal transmitter 30. Thus, the dampening effect of the pump 18 is negated.

It is also contemplated that the signal receiver 22 and the signal transmitter 30 may communicate with one another, either wirelessly or via wired connection. In particular, the transmitter 30 preferably transmits information regarding one or more characteristics of the transmitted acoustic vibration to the receiver 22. Such characteristics preferably include one or more of signal frequency (or range of frequencies), signal amplitude (or range of amplitudes), signal timing, a particular signal pattern to be transmitted, or other characteristics identifying the signal. This allows the receiver 22 to discriminate between a received signal from the transmitter 30 and noise or other extraneous vibrations in the tubing caused by, for example cross-talk between numerous transmitters and receivers in a complex infusion system, incidental contact between multiple tubes of an infusion system, vibrations induced by a pump 18, or other sources of vibration present within system 10. The receiver 22 compares the signal received at the sensor 24 with the one or more signal characteristics and, if the received signal matches the characteristics, indicates that the signal is received via the indicator 26.

While the principles of the present infusion set line tracing system have been described above in connection with specific apparatus and applications, it is to be understood that this description is made only by way of example and not as a limitation on the scope of the claims following below.

What is claimed is:

1. An acoustic line tracing system for tracing a fluid transfer system tubing line, the tracing system comprising:
    an infusion pump;
    a first acoustic receiver operably connectable to the tubing line and configured to receive a vibratory signal, the first acoustic receiver including: a first vibration sensor disposed to contact the tubing line, said first vibration sensor being configured for detecting vibration of the surface of the tubing line caused by the vibratory signal;
    a signal transmitter operatively contacting the tubing line and electrically coupled with said first acoustic receiver, said signal transmitter configured for generating acoustic vibrations in the tubing line when said first vibration sensor detects the vibratory signal; and
    wherein the first acoustic receiver is upstream from the infusion pump and the signal transmitter is downstream from the infusion pump for reducing dampening of the vibratory signal by the infusion pump.

2. The acoustic line tracing system of claim 1, further comprising:
    a second acoustic receiver connectable to the tubing line and configured for receiving the acoustic vibrations generated by said signal transmitter, said second acoustic receiver including:
    a second vibration sensor disposed to contact the tubing line, said second vibration sensor being configured for detecting vibrations in the surface of the tubing line caused by the acoustic vibrations; and
    an indicator producing at least one of an audio and a visual cue when said second vibration sensor detects the vibratory signal.

3. The acoustic line tracing system of claim 2, wherein each said vibration sensor is a piezoelectric device.

4. The acoustic line tracing system of claim 2, wherein each said vibration sensor is a microphone.

5. The acoustic line tracing system of claim 2, wherein said indicator is a light emitting diode, and wherein said diode emits light when said second vibration sensor detects the vibratory signal.

6. The acoustic line tracing system of claim 2, wherein said indicator is a speaker, and wherein said speaker emits an audible tone when said second vibration sensor detects the vibratory signal.

7. The acoustic line tracing system of claim 1, wherein said signal transmitter includes a piezoelectric device configured to generate ultrasonic acoustic vibrations.

8. The acoustic line tracing system of claim 2, wherein said signal transmitter is configured for communicating one or more characteristics of the vibratory signal to said second acoustic receiver.

9. The acoustic line tracing system of claim 8, wherein said one or more characteristics is at least one of a frequency, a range of frequencies, an amplitude, a range of amplitudes, a signal timing, and a particular signal pattern.

10. An acoustic line tracing system for verifying continuity of a tubing set in an infusion system, the line tracing system comprising:
an infusion pump;
a first acoustic receiver connectable to the tubing set and configured for receiving a vibratory signal, the first acoustic receiver including a first vibration sensor disposed to contact the tubing set, said first vibration sensor being configured for detecting vibration of the surface of the tubing set caused by the vibratory signal;
a signal transmitter operatively contacting the tubing set and electrically coupled with said first acoustic receiver, said signal transmitter configured for generating acoustic vibrations in the tubing set when said first vibration sensor detects the vibratory signal; and
wherein the infusion pump is disposed between said first acoustic receiver and said signal transmitter for reducing dampening of the vibratory signal by the infusion pump.

11. The acoustic line tracing system of claim 10, further comprising:
a second acoustic receiver connectable to the tubing set and configured for receiving the acoustic vibrations generated by said signal transmitter, said second acoustic receiver including:
a second vibration sensor disposed to contact the tubing set, said second vibration sensor being configured for detecting vibrations in the surface of the tubing set caused by the acoustic vibrations; and
an indicator producing at least one of an audio and a visual cue when said second vibration sensor detects the vibratory signal.

12. The acoustic line tracing system of claim 11, wherein each said vibration sensor is a piezoelectric device, and wherein each said vibration sensor is a microphone.

13. The acoustic line tracing system of claim 11, wherein said indicator is a light emitting diode, and wherein said diode emits light when said second vibration sensor detects the vibratory signal.

14. The acoustic line tracing system of claim 10, wherein said signal transmitter includes a piezoelectric device configured to generate ultrasonic acoustic vibrations.

15. A method for determining continuity of a tubing set comprising steps of:
providing:
a first acoustic receiver operably connectable to the tubing set and configured for receiving a vibratory signal, the first acoustic receiver including a first vibration sensor disposed to contact the tubing set, said first vibration sensor being configured for detecting vibration of the surface of the tubing set caused by the vibratory signal;
a signal transmitter operatively contacting the tubing set and electrically coupled with said first acoustic receiver, said signal transmitter configured for generating acoustic vibrations in the tubing set when said first vibration sensor detects the vibratory signal; and
wherein the first acoustic receiver is upstream from an infusion pump and the signal transmitter is downstream from the infusion pump to reduce dampening of the vibratory signal by the infusion pump.

16. The method of claim 15, further comprising:
providing a second acoustic receiver in contact with the tubing set at a first position along the tubing set, and connectable to the tubing set and configured for receiving the acoustic vibrations generated by said signal transmitter, said second acoustic receiver including a second vibration sensor operatively contacting the tubing set and configured for sensing vibrations in the tubing set, and an indicator capable of producing at least one of an audio and a visual cue when said second vibration sensor detects the vibrations;
inducing the vibratory signal at a second position along the tubing set;
detecting, by said second acoustic receiver, whether or not the vibratory signal is received at said first position along the tubing set; and
determining whether the tubing set is continuous between the first position and the second position, wherein the tubing set is determined to be continuous if said second vibration sensor detects the vibratory signal at said detecting step, wherein said indicator produces said cue when it is determined that the tubing set is continuous.

17. The method of claim 16, wherein the signal transmitter is in contact with the tubing set at said second position, said transmitter performing said inducing step.

18. The method of claim 16, further comprising steps of:
communicating one or more characteristics of the vibratory signal from said transmitter to said second acoustic receiver; and
comparing the one or more communicated characteristics with the vibratory signal received during said detecting step,
wherein said determining step determines that the tubing set is continuous if said received signal matches said one or more communicated characteristics.

19. The method of claim 16, wherein said inducing step includes manually inducing the vibratory signal by a clinician tapping the tubing set.

* * * * *